United States Patent
Hamaguchi et al.

(10) Patent No.: US 10,413,812 B2
(45) Date of Patent: Sep. 17, 2019

(54) OPERATION INFORMATION MEASUREMENT APPARATUS, GAME CONTROL PROGRAM, OPERATION INFORMATION MEASUREMENT PROGRAM

(71) Applicant: OMRON HEALTHCARE CO., LTD., Muko-shi, Kyoto (JP)

(72) Inventors: Takehiro Hamaguchi, Kyoto (JP); Yumi Kitamura, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 309 days.

(21) Appl. No.: 15/441,669

(22) Filed: Feb. 24, 2017

(65) Prior Publication Data

US 2017/0157506 A1 Jun. 8, 2017

Related U.S. Application Data (63) Continuation of application No. PCT/JP2015/073622, filed on Aug. 21, 2015.

(30) Foreign Application Priority Data

Sep. 5, 2014 (JP) .................. 2014-181374

(51) Int. Cl.
*A63F 13/211* (2014.01)
*A63F 13/428* (2014.01)
(Continued)

(52) U.S. Cl.
CPC .......... *A63F 13/211* (2014.09); *A63F 13/212* (2014.09); *A63F 13/216* (2014.09);
(Continued)

(58) Field of Classification Search
CPC .... A63F 13/211; A63F 13/212; A63F 13/216; A63F 13/31; A63F 13/428; A63F 13/58; A63F 13/825
(Continued)

(56) References Cited

FOREIGN PATENT DOCUMENTS

CN 102811780 A 12/2012
JP H11-347253 A 12/1999
(Continued)

OTHER PUBLICATIONS

Nov. 2, 2015 International Search Report issued in International Patent Application No. PCT/JP2015/073622.
(Continued)

*Primary Examiner* — Kevin Y Kim
(74) *Attorney, Agent, or Firm* — Oliff PLC (57) ABSTRACT

An operation information measurement apparatus having a detection unit for detecting information corresponding to a motion of a user includes: an operation information measurement unit that measures operation information of the user based on the information detected by the detection unit; a communication unit for performing near-field wireless communication with another operation information measurement apparatus; a determination unit that, based on a communication record of the communication unit, determines an interaction period in which the user and another user were active at the same location; and a transfer unit that transfers information relating to the interaction period determined by the determination unit to a game control unit that controls a parameter of an electronic game according to at least whether or not the interaction period exists.

21 Claims, 5 Drawing Sheets

(51) Int. Cl.
*A63F 13/216* (2014.01)
*A63F 13/825* (2014.01)
*A63F 13/212* (2014.01)
*A63F 13/58* (2014.01)
*A63F 13/31* (2014.01)
*A61B 5/11* (2006.01)

(52) U.S. Cl.
CPC ............ *A63F 13/31* (2014.09); *A63F 13/428* (2014.09); *A63F 13/58* (2014.09); *A63F 13/825* (2014.09); *A61B 5/1118* (2013.01); *A61B 5/1123* (2013.01)

(58) Field of Classification Search
USPC .......................................................... 463/39
See application file for complete search history.

(56) References Cited

FOREIGN PATENT DOCUMENTS

| | | | |
|---|---|---|---|
| JP | 2003-053024 | A | 2/2003 |
| JP | 2004-313407 | A | 11/2004 |
| JP | 2009-022440 | A | 2/2009 |
| JP | 2009-247541 | A | 10/2009 |
| JP | 2010-046347 | A | 3/2010 |
| JP | 2010-240069 | A | 10/2010 |
| JP | 2010-240070 | A | 10/2010 |
| JP | 2011-015308 | A | 1/2011 |
| JP | 2011-055915 | A | 3/2011 |
| JP | 2012-090928 | A | 5/2012 |
| JP | 2013-059659 | A | 4/2013 |
| JP | 2013-081760 | A | 5/2013 |
| JP | 2013-248482 | A | 12/2013 |

OTHER PUBLICATIONS

Dec. 9, 2016 International Preliminary Report on Patentability issued in International Patent Application No. PCT/JP2015/073622.
Jan. 25, 2019 Office Action issued in Chinese Patent Application No. 201580044899.X.

OPERATION INFORMATION MEASUREMENT APPARATUS, GAME CONTROL PROGRAM, OPERATION INFORMATION MEASUREMENT PROGRAM

TECHNICAL FIELD

The present invention relates to an operation information measurement apparatus, a game control program, and an operation information measurement program.

BACKGROUND ART

In recent years, operation information measurement apparatuses that can identify an action of a person (walking, running, going up or down stairs, sleeping, or the like) or measure an activity amount (number of steps, walking distance, expended calories, or the like) by using a motion detecting sensor that detects bodily motion, such as an acceleration sensor or an angular velocity sensor, have been actively developed. In the present specification, information on an action type and an activity amount is collectively referred to as operation information.

An operation information measurement apparatus presents operation information to a user so as to promote a desire to manage the health of the user, and it is desirable that it is used continuously every day. In view of this, it has been proposed that promotion of use of the apparatus is achieved by using information on the activity amount in a game.

For example, Patent Literatures 1 to 3 disclose pedometers that cause an electronic character to grow according to a step count. Also, Patent Literatures 4 and 5 disclose systems in which transfer of an activity amount measured by a device to a game device is enabled and the game device sets a game parameter according to the transferred activity amount and converts the activity amount into data for raising a game character.

Patent Literatures 1 to 5 use information measured by one operation information measurement apparatus in a game, but Patent Literature 6 discloses a game apparatus that uses information measured by multiple operation information measurement apparatuses.

The game apparatus disclosed in Patent Literature 6 acquires step count data measured by a pedometer as well as information on the measurement time of the step count data, and determines whether or not two or more users were walking at the same time based on the acquired information. If it is determined that two or more users were walking at the same time, bonus points are given in the game according to the number of users who were determined as walking at the same time.

CITATION LIST

Patent Literature

Patent Literature 1: JP H11-347253A
Patent Literature 2: JP 2010-240069A
Patent Literature 3: JP 2010-240070A
Patent Literature 4: JP 2004-313407A
Patent Literature 5: JP 2009-22440A
Patent Literature 6: JP 2013-248482A

SUMMARY OF INVENTION

Technical Problem

As with Patent Documents 1 to 5, by controlling a parameter of an electronic game according to the operation information, the user will exercise for the purpose of winning the game, and therefore exercise can be promoted to the user. However, since the user exercising alone is also advantageous for advancement in the game, it is difficult to promote communication with friends.

On the other hand, with the system disclosed in Patent Document 6, bonus points are obtained by multiple users walking at the same time. For this reason, an effect of promoting communication between users, as in the case of multiple users taking a walk together, can be expected. However, the system disclosed in Patent Document 6 determines that users walked at the same time according to time information associated with the step count data. For this reason, even if multiple users were exercising in different locations, bonus points are obtained, and the effect of promoting communication is small.

The present invention has been created in view of the foregoing circumstances, and it is an object thereof to provide an operation information measurement apparatus, a game control program, and an operation information measurement program according to which promotion of communication with a friend or the like can be strongly advanced.

Solution to the Problem

An operation information measurement apparatus according to the present invention is an operation information measurement apparatus having a detection unit configured to detect information corresponding to a motion of a user, including: an operation information measurement unit configured to measure operation information of the user based on the information detected by the detection unit; a communication unit for performing near-field wireless communication with another operation information measurement apparatus; a determination unit configured to, based on a communication record of the communication unit, determine an interaction period during which the user and another user were active at the same location; and a transfer unit configured to transfer information relating to the interaction period determined by the determination unit to a game control unit configured to control a parameter of an electronic game according to at least whether or not the interaction period exists.

A game control program according to the present invention is a program for causing a computer to function as the game control unit.

An operation information measurement program according to the present invention is a program for causing a computer to function as the operation information measurement unit, the determination unit, and the transfer unit in the operation information measurement apparatus.

Advantageous Effects of Invention

According to the present invention, it is possible to provide an operation information measurement apparatus, a game control program, and an operation information measurement program according to which promotion of communication with a friend or the like can be strongly advanced.

DESCRIPTION OF EMBODIMENTS

Hereinafter, an embodiment of the present invention will be described with reference to the drawings.

Figure 1:
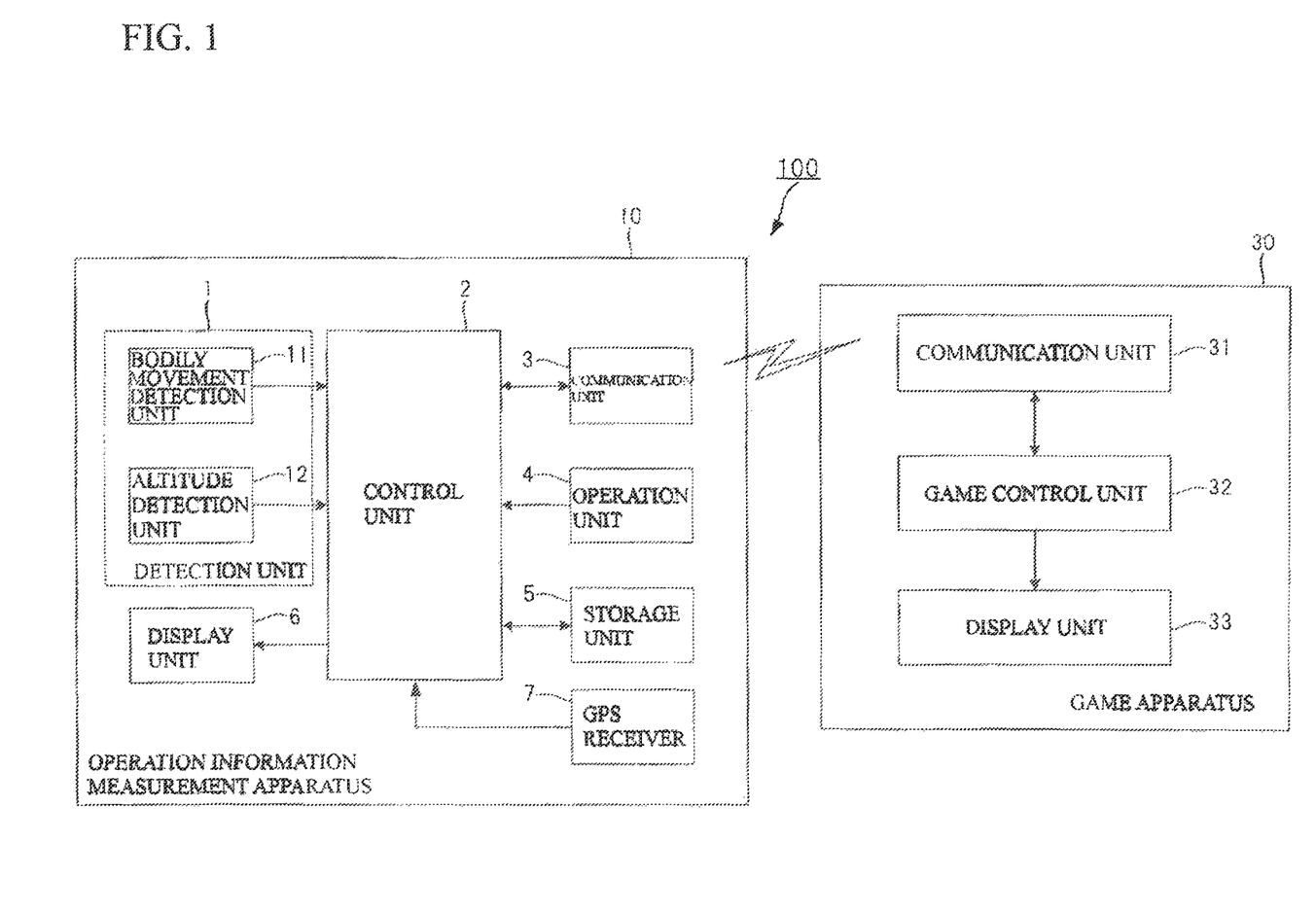
FIG. 1 is a diagram showing an overall configuration of a system 100 for describing an embodiment of the present invention.

FIG. 1 is a diagram showing an overall configuration of a system 100 for describing an embodiment of the present invention. The system 100 includes an operation information measurement apparatus 10 and a game apparatus 30. The operation information measurement apparatus 10 is used while worn on the body of a user.

The operation information measurement apparatus 10 includes a detection unit 1, a control unit 2 that performs overall control of the entire apparatus, a communication unit 3, an operation unit 4, a storage unit 5 including a storage medium such as a flash memory or a ROM (Read Only Memory), a display unit 6 for displaying various types of information, and a GPS (Global Positioning System) receiver 7.

The detection unit 1 detects information corresponding to the motion of a site on the body of the user on which the operation information measurement apparatus 10 is worn, and includes a bodily movement detection unit 11 and an altitude detection unit 12.

The bodily movement detection unit 11 detects the motion (acceleration, angular velocity, etc.) of the site on the body of the user on which the operation information measurement apparatus 10 is worn, and includes various sensors such as an acceleration sensor and an angular velocity sensor, and a signal processing unit that processes signals output from the various sensors. The bodily movement detection unit 11 need only include at least one motion sensor and a signal processing unit that processes a signal from that motion sensor.

The altitude detection unit 12 includes an air pressure sensor, and processes a detection signal from the air pressure sensor to detect the altitude of the site on which the operation information measurement apparatus 10 is worn. Note that the altitude detection unit 12 may be omitted. The altitude of the site on which the operation information measurement apparatus 10 is worn changes due to the movement of the user (e.g., transitioning from a standing position to a sitting position, or going up or down stairs). Accordingly, the information on the altitude is also information corresponding to the motion of the site on which the operation information measurement apparatus 10 is worn.

The control unit 2 is mainly constituted by a processor that executes a program stored in the ROM of the storage unit 5.

The communication unit 3 is an interface for performing near-field wireless communication with an electronic device that includes another operation information measurement apparatus 10. Near-field wireless communication refers to performing communication by means other than a network such as the Internet. A communication interface conforming to ANT, a communication interface conforming to Bluetooth, or the like is used as the interface.

The operation unit 4 is a device for inputting various types of instructions to the control unit 2, and is constituted by buttons, a touch panel mounted on the display unit 6, and the like.

The storage unit 5 stores detection information detected by the detection unit 1, stores information received via the communication unit 3, and stores information needed for the operation of the operation information measurement apparatus 10.

The GPS receiver 7 is a position information detection unit that detects position information of the operation information measurement apparatus 10. The position information detection unit may be capable of communication with a base station managed by a mobile phone company and detect the position information using the base station information.

The game apparatus 30 includes a communication unit 31, a game control unit 32, and a display unit 33.

The communication unit 31 is an interface for communicating with the communication unit 3 of the operation information measurement apparatus 10, and a near-field wireless communication interface is used thereas. Note that the operation information measurement apparatus 10 and the game apparatus 30 may be configured to be able to communicate via a network.

The game control unit 32 is constituted by a processor with a built-in memory. A game program is stored in the memory. The processor executes the game program to cause a game screen to be displayed on the display unit 33, whereby an electronic game that can be played on the game screen is provided.

Examples of the provided electronic game include a role playing game in which a character is operated and caused to grow in order to advance a story, a battling game of battling using a character, a pet-raising game that is enjoyed by causing an electronic pet to grow, a dice game, and a game in which points or the like are accumulated to clear stages or to become qualified to apply for prizes. The electronic games mentioned here are examples, and there is no limitation thereto.

Based on activity data transferred from the operation information measurement apparatus 10 via the communication unit 31, the game control unit 32 controls a parameter in the electronic game executed based on the game program. The activity data will be described later.

The game apparatus 30 may be a game-dedicated device, or an electronic device with a main function other than that of a game, such as a smartphone.

Figure 2:
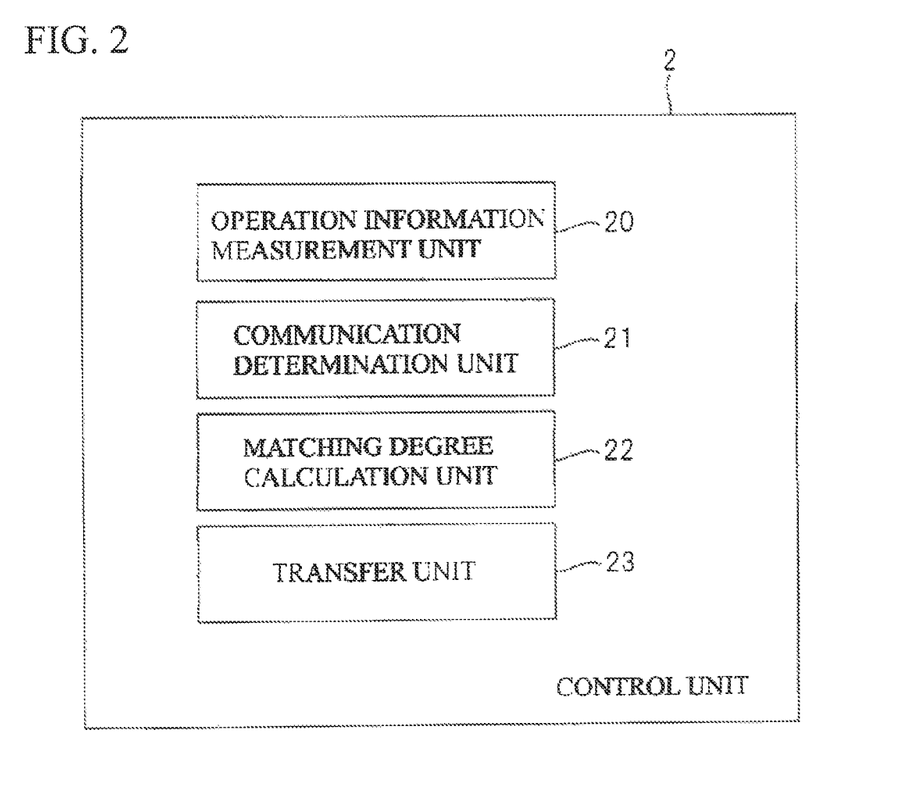
FIG. 2 is a diagram showing functional blocks that are realized by a control unit 2 due to a processor executing a program stored in a storage unit 5 of an operation information measurement apparatus 10 shown in FIG. 1.

FIG. 2 is a diagram showing functional blocks realized by the control unit 2 due to a processor executing a program stored in a storage unit 5 of an operation information measurement apparatus 10 shown in FIG. 1.

As shown in FIG. 2, the control unit 2 includes an activity information measurement unit 20, a communication determination unit 21, a matching degree calculation unit 22, and a transfer unit 23.

The operation information measurement unit 20 measures operation information of the user based on detection information detected by the detection unit 1. At least one of information on the operation type (walking, running, resting, sleeping, eating, etc.) of the user wearing the operation information measurement apparatus 10 and information on the activity amount (bodily movement amount, step count, walking distance, expended calories, etc.) of the user is included in the operation information.

The communication determination unit 21 is a determination unit that, based on a communication record of the communication unit 3, determines an interaction period, which is a period during which the user is active with another user at the same location.

When another operation information measurement apparatus 10 (hereinafter referred to as "other apparatus 10") enters a range in which the communication unit 3 of the operation information measurement apparatus 10 can communicate, communication is established between the communication unit 3 of the operation information measurement apparatus 10 and the communication unit 3 of the other apparatus 10. It is possible to use a configuration in which the operation information measurement apparatus 10 and the other apparatus 10 can effectively communicate by the communication units 3 only when there are instructions from the users. In such a case, communication between the apparatuses is established after the users of the operation information measurement apparatus 10 and the other apparatus 10 have given their consent. Alternatively, the operation information measurement apparatus 10 may have a configuration in which the communication unit 3 is always caused to operate, or it may have a configuration in which communication with a pre-registered other apparatus 10 that is the source of a communication start request is established only in the case where the other apparatus 10 has given the request.

When communication with the other apparatus 10 is established, the communication determination unit 21 acquires the identification information of the other apparatus 10 that is the communication partner. Then, in association with the identification information of the other apparatus 10, the communication determination unit 21 stores information indicating that communication with the other apparatus 10 is in progress, and information on the times at which communication was in progress. Accordingly, the storage unit 5 stores a communication record indicating the time at which communication was performed and the other apparatus 10 with which the operation information measurement apparatus 10 was communicating.

The communication unit 3 performs near-field wireless communication. For this reason, the communication determination unit 21 can check the communication record stored in the storage unit 5 to determine whether or not an interaction period during which the user (denoted as "A") of the operation information measurement apparatus 10 was being active with the user (denoted as "B") of the other apparatus 10 at the same location exists, the length of the interaction period, and the like.

It is preferable that if the length of time for communicating with the other apparatus 10, which is known from the communication record, exceeds the minimum amount of time according to which it is possible to determine that a person is interacting with another person, the communication determination unit 21 determines that an interaction period exists, and if the length of time for communicating is less than or equal to the minimum amount of time, the communication determination unit 21 determines that no interaction period of interacting with the other apparatus 10 exists. By doing so, it is possible to prevent an erroneous determination that "an interaction period exists" in the case where the user was together with another person in possession of an operation information measurement apparatus 10 for a small amount of time.

The matching degree unit 22 calculates a degree of matching between the operation information measured by the operation information measurement unit 20 in the interaction period determined based on the communication record, and the operation information measured by the operation information measurement unit 20 of the other apparatus 10 in the interaction period.

For example, the matching degree calculation unit 22 extracts the step count, which is one of the activity amounts included in the operation information, and calculates a numerical value corresponding to a difference (a numerical value inversely proportional to the difference) between the step count of the user A and the step count of the user B in the interaction period as the degree of matching.

Alternatively, based on the action type included in the operation information, the matching degree calculation unit 22 compares the action type of the user A and the action type of the user B in the interaction period and calculates a numerical value corresponding to the total amount of time (a numerical value proportional to the total amount of time) for which the action types of both users was the same, as the degree of matching.

In the communication period of communicating with the other apparatus 10 possessed by the user B, the matching degree calculation unit 22 can calculate the degree of matching by periodically acquiring the operation information measured by the other apparatus 10 via the communication unit 3 and storing the acquired operation information in the storage unit 5.

The transfer unit 23 uses data that includes information relating to the interaction period determined by the communication determination unit 21 (includes information indicating whether or not an interaction period exists, information indicating the length of the interaction period, and identification information of the communication partner in the interaction period), information on the degree of matching calculated by the matching degree calculation unit 22, and position information detected by the GPS receiver 7, as the above-described activity data, and the transfer unit 23 transfers the activity data to the game control unit 32 of the game apparatus 30 via the communication unit 3. Then, the game control unit 32 of the game apparatus 30 controls a parameter of the electronic game based on the activity data transferred from the transfer unit 23.

The parameter of the electronic game is information that contributes to advancement in the electronic game, information that contributes to removing restrictions on executing the electronic game, or the like. Examples of parameters include a time of generating an event set in the electronic game, a rate at which points used in the electronic game are given, a moving distance in the case of a virtual travel game, an ability of a character in the case of a game in which a character is used, a growth rate of an electronic pet in the case of an electronic pet game, and a rate at which points need to remove a restriction on executing the electronic game are given.

An operation of the system 100 configured as described above will be described.

Figure 3:
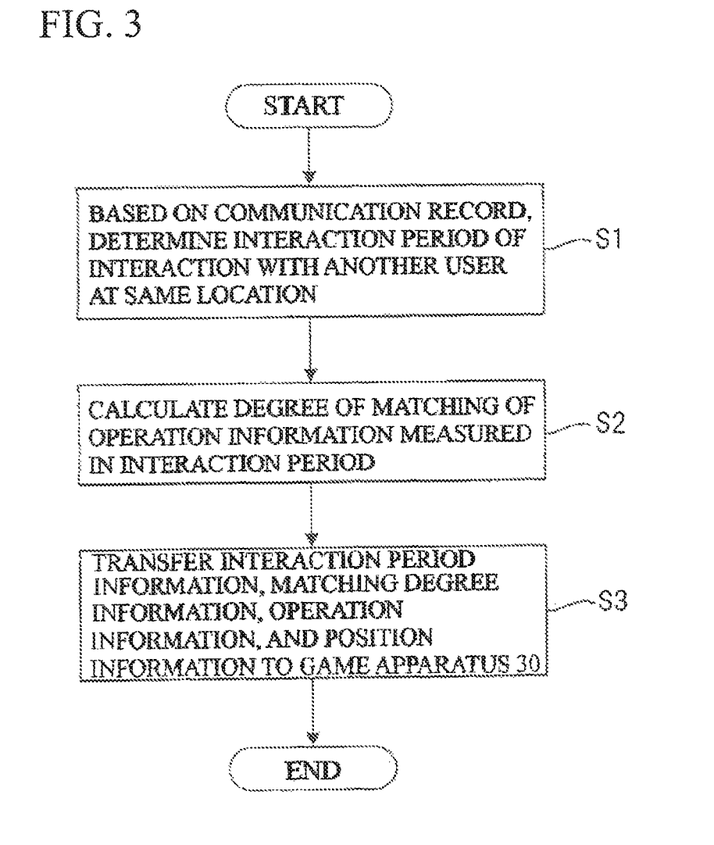
FIG. 3 is a flowchart for illustrating an operation of the operation information measurement apparatus 10 in the system 100.

FIG. 3 is a flowchart for illustrating an operation of the operation information measurement apparatus 10 in the system 100.

When the user is active while wearing the operation information measurement apparatus 10, the operation information is measured by the control unit 2, and the operation information is stored in the storage unit 5. Also, if the operation information measurement apparatus 10 performs communication with the other apparatus 10, the communication record of the communication unit 3 and the operation information measured by the other apparatus 10 are stored in the storage unit 5. If the user ends one day of activity and operates the operation unit 4 to give an instruction to transfer the activity data, the flow shown in FIG. 3 is started.

The control unit 2 reads out the communication record stored in the storage unit 5 at or after the previous time when a transfer instruction was given, and based on the read-out communication record, the control unit 2 determines the interaction period during which the user was active with another user at the same location (step S1). Upon determining the interaction period, the control unit 2 generates information indicating whether or not an interaction period exists, information indicating the period when an interaction period exists, and information relating to the interaction period including the identification information of the other apparatus 10 that is the communication partner when an interaction period exists.

If it is determined that an interaction period exists, the control unit 2 calculates the degree of matching between the operation information measured by the operation information measurement apparatus 10 in the interaction period and the operation information measured by the other apparatus 10 (step S2). If it is determined that no interaction period exists, the control unit 2 does not perform the processing of step S2.

When information relating to the interaction period and information on the degree of matching are generated, the control unit 2 transfers the activity data, which includes the operation information measured at or after the previous time when a transfer instruction was given, information relating to the interaction period generated in step S1, information on the degree of matching calculated in step S2, and position information detected by the GPS receiver 7 at or after the previous time when a transfer instruction was given, to the game apparatus 30 (step S3).

Figure 4:
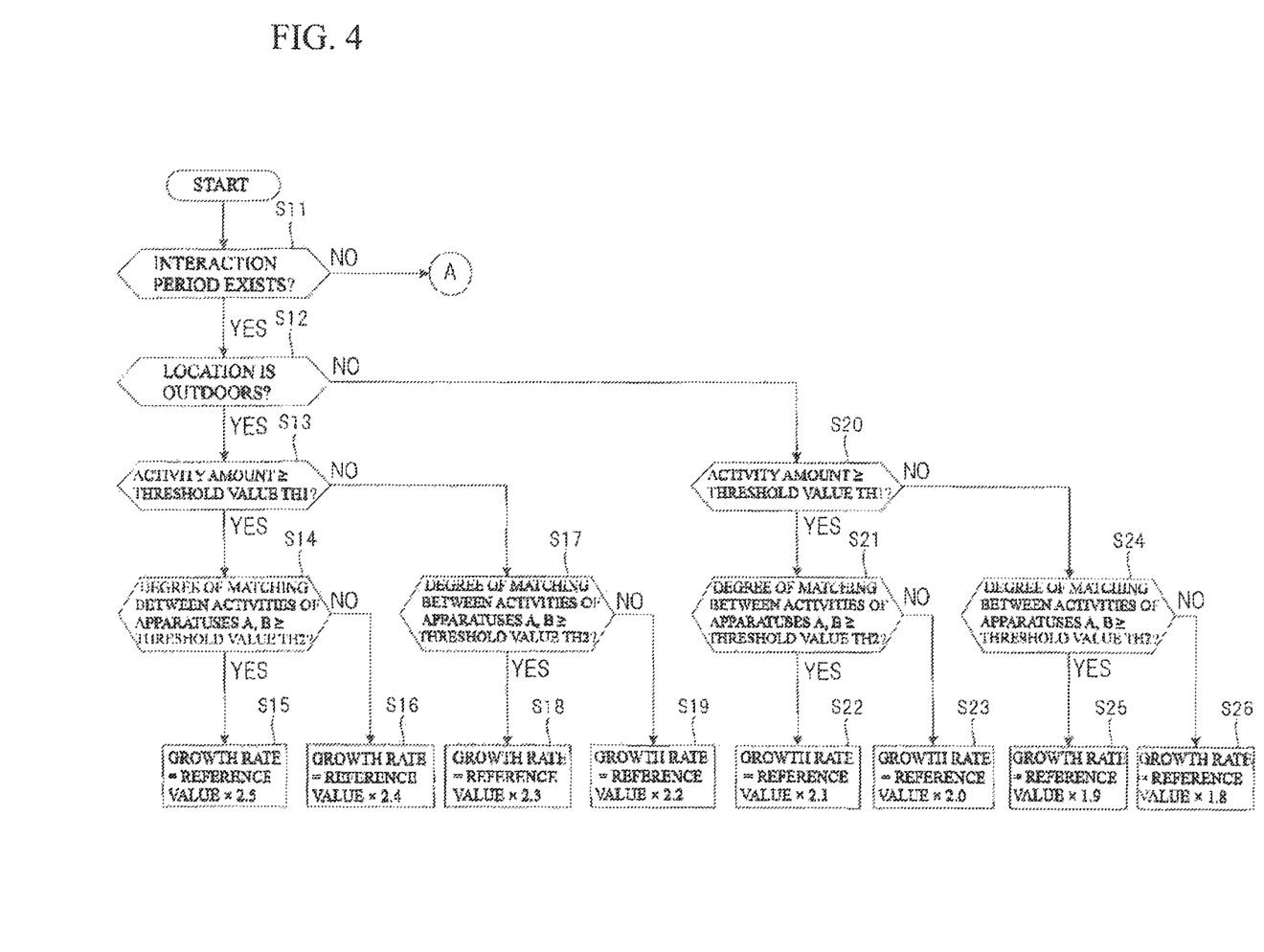
FIG. 4 is a flowchart for illustrating an operation of a game control unit 32 after receiving activity data.
Figure 5:
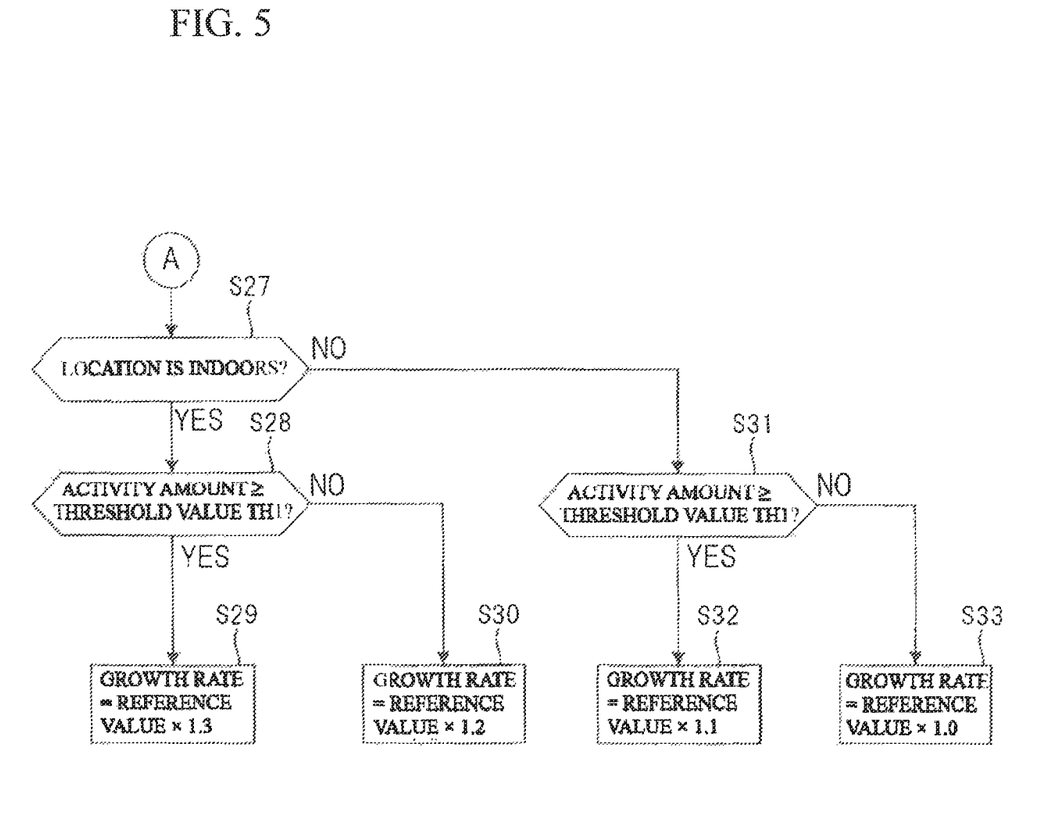
FIG. 5 is a flowchart for illustrating an operation of the game control unit 32 after receiving activity data.

FIGS. 4 and 5 are flowcharts for illustrating an operation of the game control unit 32 that has received the activity data. Hereinafter, description will be given assuming that the game apparatus 30 provides an electronic game in which a character is raised.

Based on the information relating to the interaction period included in the activity data, if no interaction period exists (step S11: NO), the game control unit 32 performs the processing of step S27 and onward in FIG. 5, and if an interaction period exists (step S11: YES), the game control unit 32 performs the processing of step S12 and onward.

In step S12, using the position information included in the activity data, the game control unit 32 checks whether the position of the operation information measurement apparatus 10 during the interaction period is indoors or outdoors. If the determination result is "outdoors" (step S12: YES), the game control unit 32 performs the processing of step S13, and if the determination result is "indoors" (step S12: NO), the game control unit 32 performs the processing of step S20.

In steps S13 and S20, the game control unit 32 determines whether or not the activity amount (e.g., step count) included in the operation information of the activity data is greater than or equal to a threshold value TH1.

If the determination of step S13 is YES, the game control unit 32 performs the processing of step S14, and if the determination of step S13 is NO, the game control unit 32 performs the processing of step S17. Also, if the determination of step S20 is YES, the game control unit 32 performs the processing of step S21, and if the determination of step S20 is NO, the game control unit 32 performs the processing of step S24.

In steps S14, S17, S21, and S24, the game control unit 32 determines whether or not the information on the degree of matching included in the activity data is greater than or equal to a threshold value TH2.

If the determination of step S14 is YES, the game control unit 32 sets the growth rate of the character, which is a parameter of the electronic game, to 2.5 times a reference value (step S15). Accordingly, the character in the electronic game grows at a speed that is 2.5 times faster than normal.

If the determination of step S14 is NO, the game control unit 32 sets the growth rate of the character, which is the parameter of the electronic game, to 2.4 times the reference value (step S16).

If the determination of step S17 is YES, the game control unit 32 sets the growth rate of the character, which is the parameter of the electronic game, to 2.3 times the reference value (step S18).

If the determination of step S17 is NO, the game control unit 32 sets the growth rate of the character, which is the parameter of the electronic game, to 2.2 times the reference value (step S19).

If the determination of step S21 is YES, the game control unit 32 sets the growth rate of the character, which is the parameter of the electronic game, to 2.1 times the reference value (step S22).

If the determination of step S21 is NO, the game control unit 32 sets the growth rate of the character, which is the parameter of the electronic game, to 2.0 times the reference value (step S23).

If the determination of step S24 is YES, the game control unit 32 sets the growth rate of the character, which is the parameter of the electronic game, to 1.9 times the reference value (step S25).

If the determination of step S24 is NO, the game control unit 32 sets the growth rate of the character, which is the parameter of the electronic game, to 1.8 times the reference value (step S26).

In step S27 of FIG. 5, based on the position information included in the activity data, the game control unit 32 determines whether or not the user A of the operation information measurement apparatus 10 was active outdoors. If the determination of step S27 is YES, the game control unit 32 performs the processing of step S28, and if the determination of step S27 is NO, the game control unit 32 performs the processing of step S31.

In step S28 and step S31, the game control unit 32 determines whether or not the activity amount (e.g., step count) included in the operation information of the activity data is greater than or equal to the threshold value TH1.

If the determination of step S28 is YES, the game control unit 32 sets the growth rate of the character, which is the parameter of the electronic game, to 1.3 times the reference value (step S29).

If the determination of step S28 is NO, the game control unit 32 sets the growth rate of the character, which is the parameter of the electronic game, to 1.2 times the reference value (step S30).

If the determination of step S31 is YES, the game control unit 32 sets the growth rate of the character, which is the parameter of the electronic game, to 1.1 times the reference value (step S32).

If the determination of step S31 is NO, the game control unit 32 sets the growth rate of the character, which is the parameter of the electronic game, to the reference value (step S33).

As described above, with the system 100, if an interaction period exists, the growth rate of the character is set to be larger than in the case where no interaction period exists. Thus, since the user can advantageously advance in the electronic game by playing with a friend, a parent, or the like, communication with a friend, a parent, or the like can be promoted. Also, since the interaction period is determined based on the communication record of the communication unit 3, it is possible to accurately determine that the user was being active with another user, and communication can be strongly promoted.

Also, with the system 100, in the case where an interaction period exists, if the location of the operation information measurement apparatus 10 during the interaction period is outdoors, the growth rate of the character is set to be higher than in the case where the location is indoors. Thus, the user can advantageously advance in the electronic game by playing outdoors with a friend or the like. For this reason, communication with a friend, a parent, or the like through exercise outdoors can be promoted, and healthy communication can be promoted.

Also, with the system 10, in the case where an interaction period exists, the greater the degree of matching of the operation information during the interaction period is, the higher the growth rate of the character is set. For example, the degree of matching of the operation information of the user A and the user B increases due to the user A and the user B playing a ball game or the like. In other words, the user can advantageously advance in the electronic game by playing with a friend while getting exercise. For this reason, communication with a friend, a parent, or the like through exercise can be promoted, and healthy communication can be promoted.

Note that in the case where an interaction period exists, based on the identification information of the other apparatus 10 possessed by the other user out of the information relating to the interaction period included in the activity data, the game control unit 32 determines whether the other user is a family member or a person other than a family member, and if the other user is not a family member, the game control unit 32 sets the growth rate higher compared to the case where the other user is a family member.

For example, a configuration is used in which identification information of any operation information measurement apparatus 10 and attribute information (information indicating whether or not a user is a family member) of the possessor of the operation information measurement apparatus 10 can be registered in advance in the game apparatus 30. Then, the game control unit 32 checks the attribute information corresponding to the identification information included in the activity data, and if the attribute information indicates a family member, the game control unit 32 sets the growth rate lower, and if the attribute information indicates a person other than a family member, the game control unit 32 sets the growth rate higher.

With this configuration, it is possible to promote communication with a person other than a family member to the user. In order to win the game, the user will actively go outside and be active, and thus it is possible to support a healthy lifestyle of the user.

Note that a case is also conceivable in which multiple pieces of identification information are included in the activity data as information relating to the interaction period. In other words, if the user of the operation information measurement apparatus is active with multiple other users in possession of other apparatuses 10, information indicating the amount of time of interaction and the users who were interacted with is included in the information relating to the interaction period.

In view of this, if it is determined in step S11 that an interaction period exists, the game control unit 32 determines the number of people who were active together during the interaction period based on the number of pieces of identification information included in the activity data. Also, it is possible to use a configuration in which the growth rate is set to be higher the greater the number of people who interacted is. Thus, since the growth rate increases due to playing with many people, it is possible to strongly promote communication to the user.

Also, when it is determined that an interaction period exists, the game control unit 32 may store identification information indicating the date of the interaction period and the interaction partners and may set the growth rate based on the identification period and the record of identification information of the interaction partners.

For example, the game control unit 32 determines how many days' worth of information indicating that an interaction period exists has been stored for a certain piece of identification information, and if the determined number of days is greater than or equal to a threshold value, the game control unit 32 sets the growth rate higher than when the determined number of days is less than a threshold value. With this kind of configuration, the greater the number of instances of playing with the same friend is, the higher the growth rate will be, and therefore communication can be strongly promoted to the user.

Note that it is possible to use a configuration in which the steps other than steps S11 and S15 in FIG. 4 are omitted and the processing of step S15 is performed when the determination of step S11 is YES. In other words, it is possible to control the parameter of the electronic game based only on whether or not an interaction period exists.

Also, it is possible to use a configuration in which steps other than steps S11, S12, S15, and S22 in FIG. 4 are omitted, step S15 is performed when the determination of step S12 is YES, and step S22 is performed when the determination of step S12 is NO. In other words, it is possible to control the parameter based on whether or not an interaction period exists and based on the activity location of the user.

Also, it is possible to use a configuration in which steps S12 and S20 to S26 in FIG. 4 are omitted, and the processing of step S13 and onward is performed when the determination of step S11 is YES. In other words, it is possible to control the parameter based on whether or not an interaction period exists, the activity amount, and the degree of matching of the operation information.

Also, it is possible to use a configuration in which steps S12, S13, S17 to S19, and S20 to S26 in FIG. 4 are omitted, and the processing of step S14 and onward is performed when the determination of step S11 is YES. In other words, it is possible to control the parameter based on whether or not an interaction period exists, and on the degree of matching of the operation information.

Also, it is possible to use a configuration in which steps S14, S16, S17, S19, S21, S23, S24, and S26 in FIG. 4 are omitted, the processing of step S15 is performed when the determination of step S13 is YES, the processing of step S18 is performed when the determination of step S13 is NO, the processing of step S22 is performed when the determination of step S20 is YES, and the processing of step S25 is performed when the determination of step S20 is NO. In other words, it is possible to control the parameter based on whether or not an interaction period exists, and on the activity amount.

Also, regarding the flow for when no interaction period exists, it is possible to omit steps S27 to S32 and perform step S33 when the determination of step S11 is NO. Alternatively, it is possible to omit steps S27 to S30 and perform step S31 and onward when the determination of step S11 is NO.

The game apparatus 30 may be capable of communication with multiple operation information measurement apparatuses 10, receive position information from the operation information measurement apparatuses 10, and generate events in the electronic game according to the number of similar pieces of position information that are received. For example, the game apparatus 30 generates an event such as the arrival of a boss character in a role playing game. Accordingly, users are encouraged to gather at the same location and play, and communication can be promoted.

It is possible to use a configuration in which the function of the game control unit 32 of the game apparatus 30 described above is included in the control unit 2 of the operation information measurement apparatus 10. Accordingly, the game can be enjoyed using the operation information measurement apparatus 10 alone.

A program for causing a computer to function as the operation information measurement unit 20, the communication determination unit 21, the matching degree calculation unit 22, and the transfer unit 23 of the operation information measurement apparatus 10 and a program for causing a computer to function as the game control unit 32 can be provided by being recorded in a computer-readable non-transitory recording medium.

Examples of such a "computer-readable recording medium" include optical mediums such as a CD-ROM (Compact Disc-ROM), and magnetic recording mediums such as a memory card. Also, such a program can be provided by downloading via a network.

The embodiments described above are to be understood as being in all ways exemplary and in no way limiting. The scope of the present invention is defined not by the above description, but by the scope of the appended claims, and all changes which come within the meaning and range of equivalency of the scope of the claims are intended to be included therein as well.

As described above, the present specification discloses the following items.

The disclosed operation information measurement apparatus is an operation information measurement apparatus having a detection unit configured to detect information corresponding to a motion of a user, including: an operation information measurement unit configured to measure operation information of the user based on the information detected by the detection unit; a communication unit for performing near-field wireless communication with another operation information measurement apparatus; a determination unit configured to, based on a communication record of the communication unit, determine an interaction period during which the user and another user were active at the same location; and a transfer unit configured to transfer information relating to the interaction period determined by the determination unit to a game control unit configured to control a parameter of an electronic game according to at least whether or not the interaction period exists.

The disclosed operation information measurement apparatus further includes a matching degree calculation unit configured to calculate a degree of matching between operation information measured by the operation information measurement apparatus possessed by the user in the interaction period determined by the determination unit, and operation information measured by the operation information measurement apparatus possessed by the other user in the interaction period, wherein the transfer unit transfers information on the degree of matching calculated by the matching degree calculation unit to the game control unit, and if the interaction period exists, the game control unit further changes the parameter according to the degree of matching.

The disclosed operation information measurement apparatus further includes a position information detection unit configured to detect position information, wherein the transfer unit transfers the position information in the interaction period determined by the determination unit to the game control unit, and if the interaction period exists, the game control unit further changes the parameter according to whether a location determined based on the position information is outdoors or indoors.

In the disclosed operation information measurement apparatus, the information relating to the interaction period determined by the determination unit includes identification information of the operation information measurement apparatus possessed by the other user, and if the interaction period exists, the game control unit changes the parameter according to whether or not the transferred identification information matches a specific piece of identification information registered in advance.

In the disclosed operation information measurement apparatus, the information relating to the interaction period determined by the determination unit includes identification information of the operation information measurement apparatus possessed by the other user, and if the interaction period exists, the game control unit changes the parameter according to the number of pieces of the transferred identification information.

The disclosed operation information measurement apparatus further includes the game control unit.

The disclosed game control program is a program for causing a computer to function as the game control unit.

The disclosed operation information measurement program is a program for causing a computer to function as the operation information measurement unit, the determination unit, and the transfer unit in the operation information measurement apparatus.

INDUSTRIAL APPLICABILITY

According to the present invention, it is possible to provide an operation information measurement apparatus, a game control program, and an operation information measurement program according to which promotion of communication with a friend or the like can be strongly advanced.

While the present invention has been described with reference to specific embodiments, the present invention is not limited to these embodiments, and many variations and modifications can be made without departing from the technical idea of the disclosed invention.

The present application claims the benefit of Japanese Patent Application 2014-181374 filed on Sep. 5, 2014, which is hereby incorporated herein in its entirety.

REFERENCE SIGNS LIST

10 Operation information measurement apparatus
1 Detection unit
2 Control unit
3 Communication unit 7 GPS receiver (position information detection unit)
20 Operation information measurement unit
21 Communication determination unit (determination unit)
22 Matching degree calculation unit
23 Transfer unit
30 Game apparatus
31 Communication unit
32 Game control unit
33 Display unit

The invention claimed is:

1. An operation information measurement apparatus having a sensor configured to detect motion information corresponding to a motion of a user, the operation information measurement apparatus comprising:
a processor programmed to:
measure operation information of the user based on the detected motion information;
perform near-field wireless communication with another operation information measurement apparatus possessed by another user;
determine, based on a communication record of the near-field wireless communication, an interaction period during which the user and another user were active at an identical location;
transfer interaction information relating to the determined interaction period to a game apparatus configured to control a parameter of an electronic game based on whether or not the determined interaction period exists; and
calculate a degree of matching between the measured operation information possessed by the user in the determined interaction period, and another operation information measured by the another operation information measurement apparatus possessed by the another user in the determined interaction period, wherein
the processor transfers information based on the calculated degree of matching to the game apparatus, and
if the determined interaction period exists, the game apparatus further changes the parameter according to the calculated degree of matching.

2. The operation information measurement apparatus according to claim 1, further comprising:
a position information sensor configured to detect position information,
wherein the processor transfers the position information in the determination interaction period to the game apparatus, and
if the interaction period exists, the game apparatus changes the parameter according to whether a location is outdoors or indoors based on the detected position information.

3. The operation information measurement apparatus according to claim 2, wherein the processor is further programmed to function as the game apparatus.

4. A non-transitory computer readable medium storing a game control program that causes a computer to function as the game apparatus according to claim 2.

5. The operation information measurement apparatus according to claim 1, wherein the processor is further programmed to function as the game apparatus.

6. A non-transitory computer readable medium storing a game control program that causes a computer to function as the game apparatus according to claim 1.

7. A non-transitory computer readable medium storing an operation information measurement program that causes a computer to function as the operation information measurement unit, the determination unit, the transfer unit, and the matching degree calculation unit in the operation information measurement apparatus according to claim 1.

8. An operation information measurement apparatus having a sensor configured to detect motion information corresponding to a motion of a user, the operation information measurement apparatus comprising:
a processor programmed to:
measure operation information of the user based on the detected motion information;
perform near-field wireless communication with another operation information measurement apparatus possessed by another user;
determine, based on a communication record of near-field wireless communication, an interaction period during which the user and another user were active at an identical location; and
transfer interaction information relating to the determined interaction period to a game apparatus configured to control a parameter of an electronic game according to at least whether or not the determined interaction period exists, wherein
the interaction information relating to the determined interaction period includes identification information of the another operation information measurement apparatus that is possessed by the another user and is a communication partner in the near-field wireless communication during the determined interaction period,
the parameter is information that contributes to advancement in the electronic game, and
if the determined interaction period exists, the game apparatus changes the parameter to enhance or improve advancement in the electronic game according to whether or not the transferred identification information matches a specific piece of identification information registered in advance.

9. A non-transitory computer readable medium storing an operation information measurement program that causes a computer to function as the operation information measurement unit, the determination unit, and the transfer unit in the operation information measurement apparatus according to claim 8.

10. The operation information measurement apparatus according to claim 8, further comprising:
a position information sensor configured to detect position information, wherein
the processor transfers the position information in the determination interaction period to the game apparatus, and
if the interaction period exists, the game apparatus changes the parameter according to whether a location is outdoors or indoors based on the detected position information.

11. The operation information measurement apparatus according to claim 10, wherein the processor is further programmed to function as the game apparatus.

12. A non-transitory computer readable medium storing a game control program that causes a computer to function as the game apparatus according to claim 10.

13. The operation information measurement apparatus according to claim 8, wherein the processor is further programmed to function as the game apparatus.

14. A non-transitory computer readable medium storing a game control program that causes a computer to function as the game apparatus according to claim 8.

15. An operation information measurement apparatus having a sensor configured to detect motion information corresponding to a motion of a user, the operation information measurement apparatus comprising:
a processor programmed to:
measure operation information of the user based on the detected motion information;
perform near-field wireless communication with another operation information measurement apparatus possessed by another user;
determine, based on a communication record of the near-field wireless communication, an interaction period during which the user and another user were active at an identical location; and
transfer interaction information relating to the determined interaction period to a game apparatus configured to control a parameter of an electronic game according to at least whether or not the determined interaction period exists, wherein
the interaction information relating to the determined interaction period includes identification information of the another operation information measurement apparatus that is possessed by the another user and is a communication partner in the near-field wireless communication during the determined interaction period,
the parameter is information that contributes to advancement in the electronic game, and
if the determined interaction period exists, the game apparatus changes the parameter to enhance or improve advancement in the electronic game according to the number of pieces of the transferred identification information.

16. The operation information measurement apparatus according to claim 15, further comprising:
a position information sensor configured to detect position information, wherein
the processor transfers the position information in the determination interaction period to the game apparatus, and
if the interaction period exists, the game apparatus changes the parameter according to whether a location is outdoors or indoors based on the detected position information.

17. The operation information measurement apparatus according to claim 16, wherein the processor is further programmed to function as the game apparatus.

18. A non-transitory computer readable medium storing a game control program that causes a computer to function as the game apparatus according to claim 16.

19. The operation information measurement apparatus according to claim 15, wherein the processor is further programmed to function as the game apparatus.

20. A non-transitory computer readable medium storing a game control program that causes a computer to function as the game apparatus according to claim 15.

21. A non-transitory computer readable medium storing an operation information measurement program that causes a computer to function as the operation information measurement unit, the determination unit, and the transfer unit in the operation information measurement apparatus according to claim 15.

* * * * *